(12) United States Patent
Morita et al.

(10) Patent No.: US 6,315,869 B1
(45) Date of Patent: Nov. 13, 2001

(54) PROCESS FOR PURIFICATION OF PERFLUOROVINYL ETHERS

(75) Inventors: Shigeru Morita; Toshihiko Amano, both of Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 09/308,592

(22) PCT Filed: Nov. 21, 1997

(86) PCT No.: PCT/JP97/04257

§ 371 Date: May 21, 1999

§ 102(e) Date: May 21, 1999

(87) PCT Pub. No.: WO98/23569

PCT Pub. Date: Jun. 4, 1998

(30) Foreign Application Priority Data

Nov. 26, 1996 (JP) ................................................ 8-314687

(51) Int. Cl.$^7$ .............................. B01D 3/34; C07C 41/42; C07C 43/17

(52) U.S. Cl. .................................. 203/57; 203/62; 203/63; 203/98; 203/58; 568/683; 568/682; 568/615; 568/677

(58) Field of Search .................... 203/62, 57, 63, 203/98, 58, 33, 38, 100; 568/615, 677, 682, 683, 687; 560/183; 526/247; 562/583, 849

(56) References Cited

U.S. PATENT DOCUMENTS

| | | | |
|---|---|---|---|
| 3,985,810 | * 10/1976 | von Halasz et al. | 560/183 |
| 4,209,635 | * 6/1980 | Munekata et al. | 560/183 |

FOREIGN PATENT DOCUMENTS

| | | |
|---|---|---|
| 47 34214 | 11/1972 | (JP) . |
| 3294242 | 12/1991 | (JP) . |
| 6 25054 | 2/1994 | (JP) . |
| 6 72938 | 3/1994 | (JP) . |

* cited by examiner

Primary Examiner—Virginia Manoharan
(74) Attorney, Agent, or Firm—Birch, Stewart, Kolasch & Birch, LLP

(57) ABSTRACT

A perfluorovinyl ether of the formula:

$$RfO(CF_2CFXO)_nCF=CF_2 \qquad (1)$$

in which Rf is a perfluoralkyl group, X is a fluorine atom or a trifluoromethyl group, and n is a number of 0 to 20 containing impurities is purified by removing a hydrogen fluoride adduct of the perfluorovinyl ether (1) through distillation, the perfluorovinyl ether (1) is distilled in the presence of a ketone or an ether having a lower boiling point than that of the perfluorovinyl ether (1) while refluxing such a solvent. This method can remove the hydrogen fluoride adduct of a perfluorovinyl ether as an impurity and provide a high purity perfluorovinyl ether.

6 Claims, 2 Drawing Sheets

PROCESS FOR PURIFICATION OF PERFLUOROVINYL ETHERS

This application is the national phase under 35 U.S.C. §371 of PCT International Application No. PCT/JP97/04257 which has an International filing date of Nov. 21, 1997 which designated the United States of America.

FIELD OF THE INVENTION

The present invention relates to a method for the purification of a perfluorovinyl ether. In particular, the present invention relates to a method for the purification of a perfluorovinyl ether by effectively separating the hydrogen fluoride adduct of a perfluorovinyl ether (hereinafter referred to as "HF adduct") or hydrogen-containing analogous compounds, which are difficult to separate from the perfluorovinyl ether by conventional methods.

Perfluorovinyl ethers are useful as the constituent monomers of tetrafluoroethylene-perfluorovinyl ether copolymers (PFA), or as the raw materials of perfluororubbers (see U.S. Pat. No. 3,132,123).

PRIOR ART

The synthesis of perfluorovinyl ethers is disclosed in U.S. Pat. No. 3,114,778, etc., and in general, perfluorovinyl ethers are prepared by pyrolyzing corresponding acid fluorides as raw materials in a gas or liquid phase. However, the HF adducts of perfluorovinyl ethers tend to be incidentally produced due to the presence of a slight amount of water in perfluorovinyl ethers prepared by the pyrolysis. In particular, in the synthesis of perfluorovinyl ethers having a high molecular weight, it is difficult to remove water by simply heating or reducing pressure, if formed salts are viscous solids. Furthermore, the reaction mixture cannot be effectively agitated, since the viscous solids adhere to agitating blades. Since the sufficient removal of water is difficult for such reasons, a large amount of HF adducts are often incidentally produced. The formation of HF adducts decreases the yield of perfluorovinyl ethers, and influences the polymerization reactions of perfluorovinyl ethers, or the physical properties of obtained polymers. Thus, the formation of HF adducts should be suppressed as much as possible in the synthesis of perfluorovinyl ethers.

Although various measures are applied, perfluorovinyl ethers, which are formed in the early stage of a reaction, often contain a relatively large amount of HF adducts due to a slight amount of water present in the reaction system.

When perfluorovinyl ethers are polymerized, HF adducts are concentrated in the unreacted perfluorovinyl ethers, which are recovered after the polymerization reaction. Thus, such recovered perfluorovinyl ethers are hardly be reused.

Among perfluorovinyl ethers, $CF_3OCF=CF_2$, $C_3F_7OCF=CF_2$, etc. can be purified by conventional rectification. However, HF adducts may not be effectively removed from $C_3F_7O(C_3F_6O)_mCF=CF_2$ in which m is 1, 2 or 3 by conventional rectification methods.

SUMMARY OF THE INVENTION

The present invention intends to provide a method for the purification of a perfluorovinyl ether by effectively separating the HF adduct of a perfluorovinyl ether or hydrogen-containing analogous compounds, which are difficult to separate from the perfluorovinyl ether by conventional methods.

Thus, the present invention provides a method for the purification of a perfluorovinyl ether of the formula:

wherein Rf is a perfluoroalkyl group having 1 to 8 carbon atoms, x, y, z and n are each a number of 0 to 20, provided that the sum of x, y, z and n is a number of 1 to 20, preferably a number of 1 to 5, comprising the step of removing a HF adduct of said perfluorovinyl ether (I) represented by the formula:

in which Rf, x, y, z and n are the same as defined above, and optionally an analogous compound of said perfluorovinyl ether represented by the formula (I) in which at least one fluorine atom is replaced with a hydrogen atom, as impurities, wherein said perfluorovinyl ether (I) is distilled in the presence of at least one solvent selected from the group consisting of ketones and ethers having a lower boiling point than that of said perfluorovinyl ether (I) while refluxing said solvent.

DETAILED DESCRIPTION OF THE INVENTION

Figure 1:
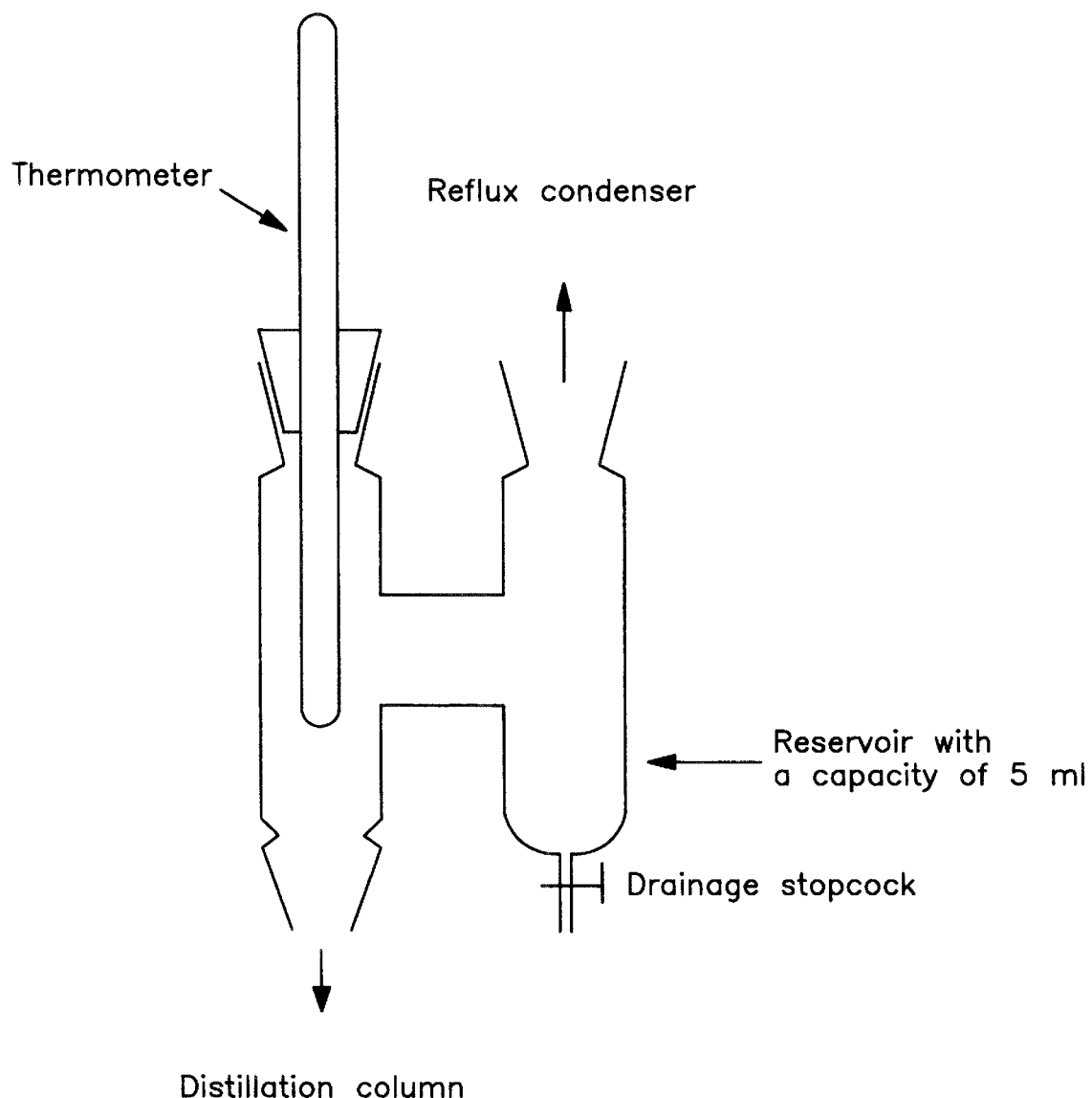
FIG. 1 is a schematic view of a refluxing condenser used in Example 1.

The perfluorovinyl ethers (I) containing impurities, which are subjected to the purification method of the present invention may be of any origin. For example, the initial distillate of crude perfluorovinyl ethers obtained by pyrolysis, or perfluorovinyl ethers which are recovered after the polymerization of the perfluorovinyl ethers (I) can be purified by the purification method of the present invention.

Ketones or ethers used in the purification method of the present invention have a boiling point lower than that of the perfluorovinyl ether (I) to be purified. That is, any ketones or ethers can be used insofar as they satisfy this requirement for boiling points. Specific examples of the solvents include acetone, methyl ethyl ketone (MEK), methyl isobutyl ketone (MIBK), tetrahydrofuran (THF), etc.

The purification is carried out by distilling the perfluorovinyl ether (I) containing impurities in the presence of a ketone or an ether which satisfies the above requirement for a boiling point.

The HF adduct of the perfluorovinyl ether (I) is more easily dissolved in such ketones or ethers than the perfluorovinyl ether (I) on one hand, and on the other hand, the perfluorovinyl ether (I) and such ketones or ethers cannot inherently be mixed in any ratio but they form two phases. Thus, they can be distilled at a temperature lower than their boiling temperatures based on the principle known as a steam distillation. Accordingly, when the perfluorovinyl ether (I) is distilled in the presence of such ketones or ethers, the HF adduct of the perfluorovinyl ether (I) is extracted with the ketones or ethers from the perfluorovinyl ether (I), and the perfluorovinyl ether (I) is purified.

In addition, when the vapor of the solvent containing the HF adduct is cooled and liquefied, the solvent and HF adduct spontaneously separate. In many cases, the perfluorovinyl ether (I) forms a lower layer, since the specific gravity of the perfluorovinyl ether (I) is larger than that of the ketone or ether.

A method is known to remove water, which generally forms in an esterification process, by azeotropic distillation. When a ketone or an ether is spontaneously refluxed with the same apparatus as that used in such azeotropic distillation, the ketone or ether can be allowed in contact with the perfluorovinyl ether (I) in a counter-current manner, and the impurities can be effectively extracted.

The distillation rate of the perfluorovinyl ether (I) is determined by the boiling points of the perfluorovinyl ether (I) and solvents. Thus, solvents having a higher boiling point are advantageous to increase the distillation rate of the perfluorovinyl ether (I) while solvents having a lower boiling point are preferable from the viewpoint of the efficiency of impurity removal. Alternatively, the efficiency of impurity removal can be improved by increasing the number of plates of a distillation column.

The kind of a solvent is determined based on the purity of the perfluorovinyl ether (I) prior to purification, and the intended purity of the perfluorovinyl ether (I) after the purification. In general, the kind of a solvent is selected so that the concentration of impurities is decreased to less than 1% after the purification from 1 to 20% prior to the purification. Preferably, solvents having a boiling point which is 30° C. to 50° C. lower than that of the perfluorovinyl ether (I) are used.

The amount of a ketone or an ether depends on the amounts of the HF adduct and/or hydrogen-substituted analogous compounds, and may be usually from 1 to 100 wt. parts, preferably from 5 to 50 wt. parts, per 100 wt. parts of the perfluorovinyl ether (I).

The purified perfluorovinyl ether (I) contains several wt. % to less than 20 wt. % of a ketone or an ether, but such a ketone or an ether can be easily removed by washing and/or distillation.

When the amount of a ketone or an ether which is used in the initial step is small, the necessary amount of ketones or ethers should be supplemented during the purification process, since a part of a ketone or an ether is removed outside the purification system as the purification proceeds. The solvents may be supplemented through the head or still of a distillation column, but should be carefully supplemented not to disturb the distillation conditions. When the solvent is supplement through the head of a distillation column, the conditions are the same as those in conventional extractive distillation processes.

It is known that the perfluorovinyl ether (I) is pyrolyzed or isomerization polymerized, when the still temperature of a distillation column exceeds 100° C., in particular, 150° C. Thus, the still temperature is preferably maintained as low as possible. For example, the sill temperature is 150° C. or lower, preferably 110° C. or lower.

The purification method of the present invention may be carried out under reduced pressure, if required. When the perfluorovinyl ether (I) having a boiling point of about 100° C. to 150° C. is purified, MIBK is preferably used, since the above temperature conditions are spontaneously satisfied under atmospheric pressure.

EXAMPLES

The present invention will be illustrated by the following Examples, which do not limit the scope of the present invention in any way.

Herein, the content (wt. %) of a HF adduct is calculated according to the formula:

[HF adduct weight/(HF adduct weight+perfluorovinyl ether weight)]×100, unless otherwise defined.

EXPERIMENT 1

A VE (perfluorovinyl ether) raw material was allowed in intimate contact with the same volume of a solvent at 30° C., and the composition of each layer was analyzed by gas chromatography. The results are shown in Table 1.

The ratio of the HF adduct to VE in such solvents was larger than that in the VE raw material. Thus, it can be seen that the HF adduct was selectively dissolved in the solvents. In Table 1, "DIOX" stands for dioxane.

TABLE 1

Selective extraction of a HF adduct from $C_3H_7O(C_3F_6O)_2CF=CF_2$ with various solvents

|  | Percentages (%) in solvent | | Percentages (%) of VE and HF adduct | |
| --- | --- | --- | --- | --- |
|  | VE | HF adduct | VE | HF adduct |
| VE raw material | 87.34 | 11.73 | 88.16 | 11.84 |
| Acetone | 1.39 | 0.76 | 64.61 | 35.39 |
| MEK | 1.48 | 0.71 | 67.53 | 32.47 |
| MIBK | 2.38 | 1.07 | 69.06 | 30.94 |
| THF | 1.33 | 0.54 | 71.02 | 28.98 |
| DIOX | 0.13 | 0.06 | 67.37 | 32.63 |

EXPERIMENT 2

A VE raw material (50 ml) and a solvent (50 ml) were charged in a 200 ml flask, and mildly refluxed under atmospheric pressure while stirring, and distillates were condensed at the head of the flask. The lower layer was recovered step by step, while the whole amount of the upper layer was recycled. The results are shown in Table 2.

In Table 2, the distillation rate of VE means the, relative value of a recovering rate of VE when an evaporation rate is maintained substantially the same. It can be seen from the results of Table 2 that the mixture boils at a temperature lower than the boiling points of VE and a solvent. It can also be seen that the distillation rate of VE is higher, when the boiling point of a solvent is higher.

Table 2

Azeptropic distillation of $C_3H_7O(C_3F_6O)_2CF=CF_2$ (having a boiling point of 151° C.) with various solvents (small scale)

TABLE 2

| Solvent | Boiling point of solvent (° C.) | Distillation temperature (° C.) | Distillation rate of VE |
| --- | --- | --- | --- |
| Acetone | 57 | 56 | 0.08 |
| MEK | 79.53 | 76 | 0.25 |
| MIBK | 116.7 | 106.5 | 1.0 |

EXPERIMENT 3

A VE raw material containing a methyl ester was allowed in intimate contact with the same volume of a solvent at 30° C., and the composition of each layer was analyzed by gas chromatography. The results are shown in Table 3.

In such a solvent, the ratio of the methyl ester to VE was larger than that in the VE raw material. Thus, it can be seen that the methyl ester is selectively dissolved in the solvent.

TABLE 3

Selective extraction of $C_3F_7O(C_3F_6O)_2CF(CF_3)COOCH_3$ with MEK from $C_3H_7O(C_3F_6O)_2CF=CF_2$

|  | Percentages (%) in solvent | | Percentages (%) of VE and methyl ester | |
|---|---|---|---|---|
|  | VE | Methyl ester | VE | Methyl ester |
| VE (methyl ester) | 96.03 | 3.08 | 96.90 | 3.11 |
| MEK | 1.47 | 0.46 | 75.06 | 24.94 |

COMPARATIVE EXAMPLE 1

$C_3H_7O(C_3F_6O)_2CF=CF_2$ containing 27 wt. % of a HF adduct was fully refluxed in a rectification column having the number of plates of 20 for 3 hours. The content of the HF adduct in a mixture at the head of the column was 23 wt. %.

EXAMPLE 1

$C_3H_7O(C_3F_6O)_2CF=CF_2$ containing 11.84 wt. % of a HF adduct (50 ml), to which acetone (50 ml) had been added, was charged in the still of a Vigreux distillation column having a body length of 20 cm which was equipped with a refluxing condenser shown in FIG. 1. Then, the sill was heated to 56° C. to distill the perfluorovinyl ether. The distillate was recovered from the liquid reservoir of the refluxing condenser, whenever about 5 ml of the perfluorovinyl ether accumulated in the reservoir, and the composition of the distillate was analyzed by gas chromatography. The contents of the HF adduct in the distillates were between 2.04% and 3.18% (the first to ninth recoveries), and the content of the HF adduct in the liquid remaining in the still was 78.12%.

EXAMPLE 2

The perfluorovinyl ether was purified in the same manner as in Example 1 except that a Vigler distillation column having a body length of 40 cm was used. The distillates were analyzed. The results are as follows:

| Distillate No. | Content of HF adduct (%) |
|---|---|
| 1 | 0.52 |
| 2 | 0.65 |
| 3 | 1.02 |
| 4 | 1.16 |
| 5 | 1.18 |
| 6 | 1.36 |
| 7 | 1.33 |
| 8 | 1.98 |
| 9 | 4.35 |
| (Still | 87.7) |

EXAMPLE 3

The perfluorovinyl ether was purified in the same manner as in Example 1 except that MEK was used in place of acetone, and a spiral tube having a height of 40 cm and the number of windings of 20 was used in place of the Vigler distillation column. The distillates were analyzed. The results are as follows:

| Distillate No. | Content of HF adduct (%) |
|---|---|
| 1 | 0 |
| 2 | 0 |
| 3 | 0.015 |
| 4 | 0.33 |
| 5 | 0.78 |
| 6 | 4.10 |
| (Still | 99.37) |

EXAMPLE 4

The perfluorovinyl ether was purified in the same manner as in Example 3 except that a rectification column having the number of plates of 15 was used in place of the spiral tube, and 1 kg of $C_3H_7O(C_3F_6O)_2CF=CF_2$ was charged. No HF adduct was found in the distillates.

EXAMPLE 5

Figure 2:
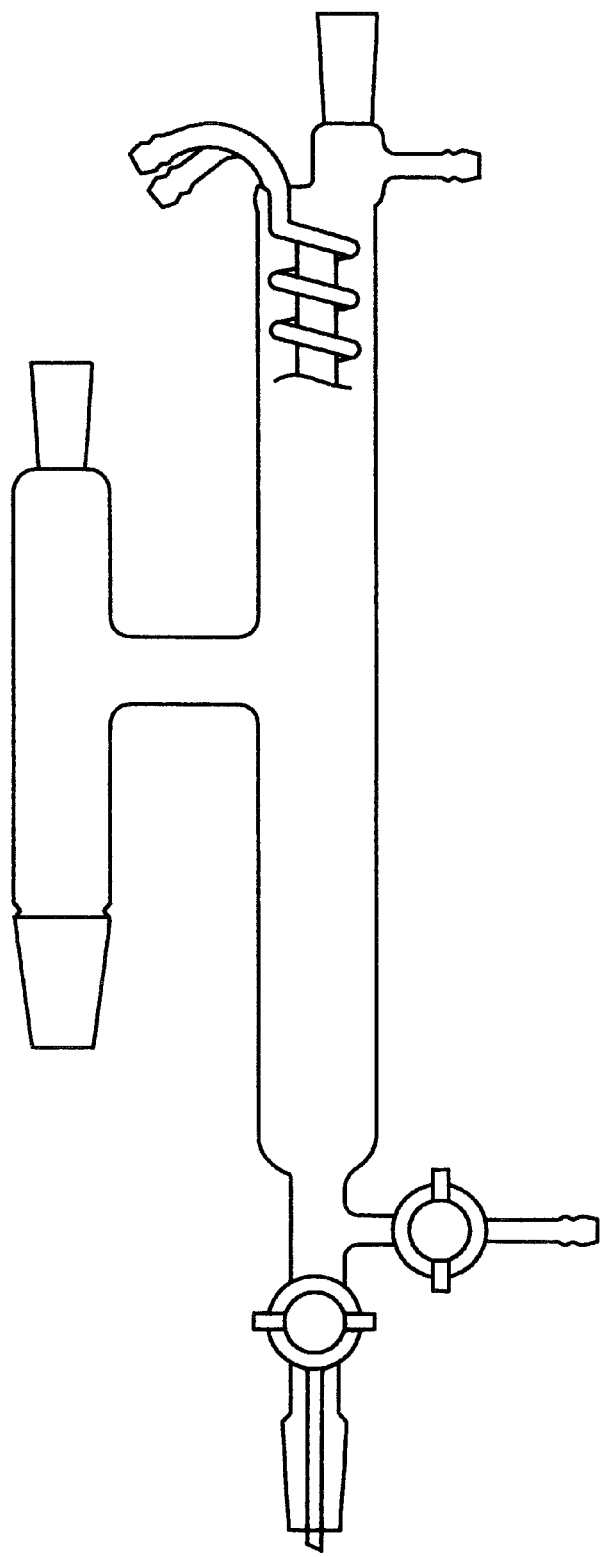
FIG. 2 is a schematic view of a head used in Example 5.

The perfluorovinyl ether was purified in the same manner as in Example 1 except that a head shown in FIG. 2 was assembled, and attached to a Vigler distillation column having a body length of 80 cm, and MIBK was used as a solvent.

$C_3H_7O(C_3F_6O)_2CF=CF_2$ containing 8.6% of a HF adduct (8.1 kg) and MIBK (4 liters) were charged into a 10 liter flask equipped with a stirrer, and heated to reflux while stirring. An amount of $C_3H_7O(C_3F_6O)_2CF=CF_2$ collected in the head was recovered step by step, and about 4.5 liters of $C_3H_7O(C_3F_6O)_2CF=CF_2$ in total was recovered over 15 hours.

The recovered $C_3H_7O(C_3F_6O)_2CF=CF_2$ was washed with acetone and then with pure water to obtain 6.8 kg of $C_3H_7O(C_3F_6O)_2CF=CF_2$ (HF adduct content: 0.6%; pure ether: 99.4%).

What is claimed is:

1. A method for the purification of a perfluorovinyl ether of the formula:

$$RfO(CF_2O)_x(CF_2CF_2O)_y(CF_2CF_2CF_2O)_z(CF(CF_3)CF_2O)_nCF=CF_2 \quad (I)$$

wherein Rf is a perfluoroalkyl group having 1 to 8 carbon atoms, x, y, z and n are each a number of 0 to 20, provided that the sum of x, y, z, and n is a number of 1 to 20, wherein said perfluorovinyl ether contains impurities, comprising the step of removing as an impurity a hydrogen fluoride adduct of said perfluorovinyl ether (I) represented by the formula:

$$RfO(CF_2O)_x(CF_2CF_2O)_y(CF_2CF_2CF_2O)_z(CF(CF_3)CF_2O)_nCFHCF_3 \quad (II)$$

in which Rf, x, y, z and n are the same as defined above,
   wherein said perfluorovinyl ether (I) containing impurities is distilled in the presence of at least one solvent selected from the group consisting of ketones and ethers having a lower boiling point than that of said perfluorovinyl ether (I) while refluxing said solvent.

2. A method according to claim 1, wherein said perfluorovinyl ether containing impurities is an initial distillate of a crude perfluorovinyl ether obtained by pyrolysis.

3. A method according to claim 1, wherein said perfluorovinyl ether containing impurities is a recovered perfluorovinyl ether after polymerization of said perfluorovinyl ether.

4. A method according to claim 1, wherein said impurities optionally contain an additional analogue compound of a perfluorovinyl ether of the formula (I) in which at least one fluorine atom is replaced with a hydrogen atom.

5. A method according to claim 1, wherein said at least one solvent has a boiling point which is 30° C. to 50° C. lower than that of perfluorovinyl ether (I).

6. A method according to claim 1, wherein said at least one solvent is selected from the group consisting of acetone, methyl ethyl ketone, methyl isobutyl ketone, tetrahydrofuran and dioxane.

* * * * *